(12) United States Patent
Jönsson

(10) Patent No.: US 8,765,639 B2
(45) Date of Patent: Jul. 1, 2014

(54) ALKOXYLATED ASYMMETRIC ALKYLAMINE SURFACTANTS AS ADJUVANTS

(75) Inventor: Claes Johan Markus Jönsson, Malmö (SE)

(73) Assignee: Akzo Nobel N.V., Arnhem (NL)

( * ) Notice: Subject to any disclaimer, the term of this patent is extended or adjusted under 35 U.S.C. 154(b) by 703 days.

(21) Appl. No.: 12/667,331

(22) PCT Filed: Jul. 3, 2008

(86) PCT No.: PCT/EP2008/058542
§ 371 (c)(1),
(2), (4) Date: Mar. 4, 2010

(87) PCT Pub. No.: WO2009/004044
PCT Pub. Date: Jan. 8, 2009

(65) Prior Publication Data
US 2010/0204047 A1  Aug. 12, 2010

Related U.S. Application Data

(60) Provisional application No. 60/978,205, filed on Oct. 8, 2007.

(30) Foreign Application Priority Data

Jul. 5, 2007  (EP) .................................... 07013199

(51) Int. Cl.
*A01N 39/02* (2006.01)
*A01N 47/28* (2006.01)

(52) U.S. Cl.
USPC .......................................... 504/145; 504/323

(58) Field of Classification Search
USPC ................................ 504/145, 323
See application file for complete search history.

(56) References Cited

U.S. PATENT DOCUMENTS

| 3,276,856 A | 10/1966 | Esposito |
| 2005/0215434 A1 | 9/2005 | Ruiz et al. |

FOREIGN PATENT DOCUMENTS

| CA | 1242719 | * 10/1988 |
| WO | WO 00/64257 | * 11/2000 |

OTHER PUBLICATIONS

Glennie et al. J. Disp. Sci. Tech. 2006, 27 (5), 731-738; published: Sep. 2006.*
International Search Report for International Application No. PCT/EP2008/058542, Aug. 12, 2008.
L.L. Jansen, Weeds (1965) 13(2), 123-130 (XP-0024803075).
Ullmann's Encyclopedia of Industrial Chemisty 6th edition Chapter 7, "Chemical Control of Weeds" Part 7.2.1, Dec. 2002.

* cited by examiner

*Primary Examiner* — Gina C Justice
*Assistant Examiner* — Genevieve S Alley
(74) *Attorney, Agent, or Firm* — Norris McLaughlin & Marcus, P.A.

(57) ABSTRACT

The present invention generally relates to a herbicidal formulation that comprises at least one phenoxy acid herbicide or an agriculturally acceptable salt or derivative thereof, and a surfactant adjuvant, wherein said surfactant adjuvant comprises at least one alkoxylated asymmetric alkylamine surfactant having the formula (I) wherein R1 is a straight or branched chain, saturated or unsaturated hydrocarbyl group having from 8 to 24 carbon atoms; R2 is a C1-C4 alkyl group or a benzyl group; A is an alkylene group containing from 2-4 carbon atoms; x is 1-30; and y is 0-10; or a quaternised derivative of (I) having the formula (II) wherein R1 is a straight or branched chain, saturated or unsaturated hydrocarbyl group having from 8 to 24 carbon atoms; R2 is a C1-C4 alkyl group or a benzyl group; A is an alkylene group containing from 2-4 carbon atoms; x is 1-30; y is 0-10; R3 is a C1-C4 alkyl group; and Y$^-$ is an anion. The invention also relates to a method for controlling unwanted vegetation which comprises applying an effective amount of the aforementioned herbicidal formulation to said unwanted vegetation.

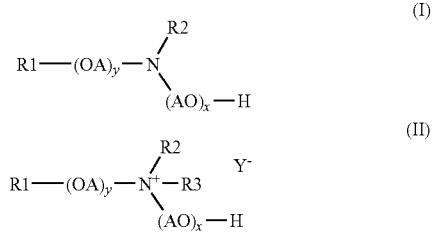

23 Claims, 1 Drawing Sheet

ALKOXYLATED ASYMMETRIC ALKYLAMINE SURFACTANTS AS ADJUVANTS

FIELD OF THE INVENTION

The present invention relates to pesticide formulations, in particular, phenoxy acid formulations comprising alkoxylated asymmetric alkylamine surfactants as adjuvants.

BACKGROUND OF THE INVENTION

Phenoxy acid herbicides are members of a family of chemicals related to the growth hormone indoleacetic acid (IAA). When sprayed on a field of crops such as wheat, rice or corn (monocots), phenoxy acid herbicides selectively induce rapid, uncontrolled growth in broad-leaf weeds (dicots) that eventually kills the unwanted vegetation and leaves the crops relatively unaffected. Phenoxy acid herbicides were independently developed in the USA and UK during World War II and were first introduced commercially in 1946. Today, 60 years later, the phenoxy acid herbicides still remain among the most widely used herbicides in the world.

There is a wide variety of phenoxy acid herbicides in use, further grouped into the phenoxyacetic, phenoxybutyric, and phenoxypropionic subtypes, the last itself containing the aryloxyphenoxypropionic subtype, which has the greatest number of commercial variants.

2,4-D (2,4-dichlorophenoxyacetic acid) is one well-known example of a phenoxy acid herbicide. The present invention will be exemplified using this herbicide, though the other phenoxy acids can equally well be used in the same types of formulations for the same purposes. 2,4-D acid is a white, crystalline solid, minimally soluble in water, generally formulated as soluble concentrates or emulsifiable concentrates in order to facilitate its application. The soluble concentrates are usually non-volatile, water-soluble formulations of 2,4-D amine salts such as dimethylamine, isopropylamine, triethylamine, or diethanolamine salts. The emulsifiable concentrates are formulations of, for example, 2,4-D esters with high volatility, such as ethyl, propyl, isopropyl, butyl, isobutyl, or amyl esters, or 2,4-D esters with low volatility, such as butoxyethyl or 2-ethylhexyl esters.

When the term "ammonium" is used herein to refer to salts of phenoxy acids, this term applies strictly to inorganic ammonium, i.e., $NH_4^+$, unless the context demands otherwise. Phenoxy acid rates and concentrations given herein, even where the phenoxy acid is present as a salt or salts, are expressed as acid equivalent (ae)—by acid equivalent is meant that portion of a formulation that, theoretically, could be converted back to the parent acid and represents the original acid portion of the molecule—unless the context demands otherwise.

It has been generally accepted that, with the same 2,4-D acid equivalent, the 2,4-D esters are more effective than the 2,4-D amine salts, although their herbicidal effect is slower. The highly volatile esters are also more effective than esters with low volatility, but can cause undesired damage to the surrounding environment because of their volatility. The risk of unwanted damage caused by volatilisation has caused the application of highly volatile ester formulations to be regulated and restricted.

A commonly practised way to enhance the performance of pesticide products is to add an adjuvant either to the pesticide formulation or to the spray tank just before application. An adjuvant can maximise the activity of the pesticide product by a variety of functions, such as increasing spray droplet retention on difficult to wet leaf surfaces, or facilitate penetration of the pesticide into the plant cuticle. It is noted that not all adjuvants work the same way and depending on the adjuvant chosen, a certain herbicide will have a specific efficacy. Therefore for the various herbicides specific combinations with selected adjuvants have been developed and marketed.

Substances traditionally utilised as adjuvants are, for example, petroleum or natural based oils, inorganic salts, polymers, polyols, and surfactants. Surfactants have proved to be very useful and versatile adjuvants for many applications, but selecting the optimum surfactant system and the optimum concentration for a specific pesticide application is often a challenge. More specifically, as is well-known in the art, only particular surfactants work efficiently with specific herbicides. This is very clear from Ullmann's Encyclopedia of Industrial Chemistry $6^{th}$ edition (Wiley Interscience; electronic edition) Chapter 7, "Chemical Control of Weeds" Part 7.2.1, which says "Intensive research with surfactants has usually shown that a particular surfactant is ideal for a specific herbicide on a particular species. This of course greatly complicates the problems involved in making recommendations for herbicides that might be used on a wide range of weed species. As a result, recommendations usually refer to a small number of common surfactants shown to be reasonably effective over a wide range of herbicides and species. Household detergents are designed for an entirely different purpose, and are usually considerably less effective as adjuvants for herbicide sprays."

Specific amines that have proven to be useful as a pesticide adjuvant are amines with a primary, secondary or tertiary amine function which react with an acid to form a salt. By using an amine surfactant to neutralise all, or a part of, the 2,4-D acid, it is possible to create a highly concentrated, water-soluble 2,4-D formulation with a built-in adjuvant system.

U.S. Pat. No. 3,276,856 discloses compositions containing dimethyl-($C_{12}$-$C_{18}$ alkyl)amine salts of phenoxy acid herbicides, e.g. 2,4-dichlorophenoxyacetic acid. These compositions have a high level of active herbicidal ingredient and improved emulsification properties, and are used to make water-in-oil emulsions.

US 2005/0215434 teaches to use herbicidal 2,4-D-amine salts, e.g. dimethylamine or diethanolamine salts, in combination with a humectant, such as ethoxylated fatty amines or amine oxides, an anti-freeze, and an anti-foaming agent in order to make liquid compositions that are non-volatile, soluble in water, and stable at low temperatures.

WO 00/64257 discloses various amine-containing surfactants—herbicide combinations, but not the alkoxylated asymmetric amines according to the invention.

In an article by L. L. Jansen in *Weeds* (1965), 13(2), 123-130, various amine salts of 2,4-dichlorophenoxyacetic acid are disclosed and their herbicidal activity investigated by greenhouse evaluation. Fatty amines, such as coco, soya, oleyl, and tallow alkylamine, were used as such or as ethoxylated or propoxylated derivatives. Further amine derivatives used were di(long chain alkyl) amines, such as di-coco and di-(H-tallow alkyl)amine, tertiary amines such as methyl-di-(coco alkyl)amine and dimethyl-(coco alkyl)amine, and N-alkyl-1,3-propane-diamines, such as N-oleyl-1,3-propanediamine and N—($C_{19}$ alkyl)-N,N'-diethyl-1,3-propanediamine. The salts were used in water and/or oil.

As disclosed by Jansen, alkylamine based adjuvants have been used in the past and have proven to have bioefficacy enhancing ability in regard of 2,4-D. The choice of surfactant can be important, since there are wide variations among surfactants in terms of their ability to enhance the herbicidal efficacy of phenoxy acids for particular applications. The class of surfactants known as alkylamine ethoxylates has been found particularly useful in providing enhanced efficacy to phenoxy acids. One representative alkylamine surfactant is tallowamine di-ethoxylate with 15 EO, as represented by the following chemical structure:

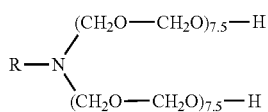

However, the use of these kinds of ethoxylated alkylamines as adjuvants is under scrutiny in many jurisdictions due to their unfavourable biodegradation rating, and finding a suitable adjuvant with good environmental properties in addition to a good efficacy enhancing property is difficult.

Accordingly, it is desired to develop a stable aqueous phenoxy acid salt formulation (i) having high phenoxy acid ae loading, (ii) which is stable and provides better efficacy than that of commercial phenoxy acid salt formulations, (iii) and which has an overall better biodegradability than formulations utilising present adjuvants.

These and other objectives are met by the adjuvants and herbicidal formulations of the present invention.

SUMMARY OF THE INVENTION

The present invention relates to specific phenoxy acid formulations comprising, as a very specific adjuvant, at least one alkoxylated asymmetric alkylamine surfactant. It was found that such systems have good biodegradation. As used in this application, the term alkoxylated asymmetric alkylamine means an alkoxylated amine having three different groups connected to the nitrogen atom, where one of the groups is a polyalkyleneoxy group, another is an, optionally substituted, alkyl or alkenyl group, and the last one is a smaller hydrocarbyl group. The invention also pertains to quaternised derivatives of the alkoxylated asymmetric alkylamines.

DETAILED DESCRIPTION OF THE INVENTION

Figure 1:
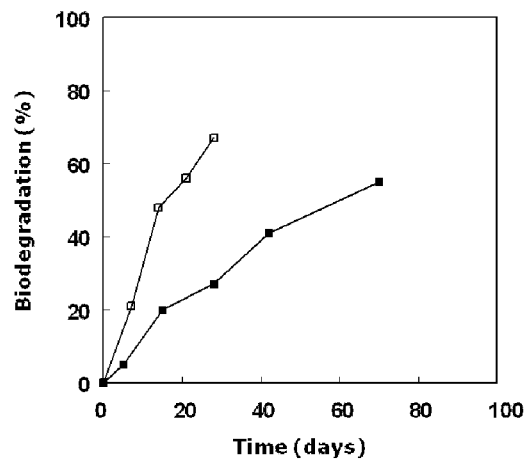
FIG. 1 is a graph showing percentages of biodegradation of Polyoxyethylene (15) coco amine (reference) and Polyoxyethylene (15) alkyl(C12-14) methylamine plotted versus time in an embodiment.

The present invention relates to pesticide formulations, in particular, phenoxy acid formulations comprising alkoxylated asymmetric alkylamine surfactants as adjuvants. More particularly, we found that certain asymmetric alkylamine alkoxylates not only provided enhanced bioefficacy to phenoxy acid formulations, but also a favourable biodegradability profile. The present invention also makes it possible to develop stable aqueous ammonium, alkylammonium, potassium or mixed salts phenoxy acid compositions, preferably ammonium or alkylammonium phenoxy acid compositions, which have high ae loading, are stable, provide better efficacy than that of commercial standard phenoxy salt formulations, and which have good biodegradation.

The class of alkoxylated asymmetric alkylamine surfactants useful in the context of the present invention is represented by the following formula:

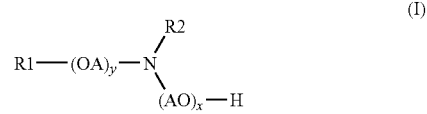

wherein R1 is a straight or branched chain, saturated or unsaturated hydrocarbyl group having from 8 to 24 carbon atoms; R2 is a C1-C4 alkyl group or a benzyl group; A is an alkylene group containing from 2-4 carbon atoms, preferably 2 carbon atoms; x is 1-30; y is 0-10; or a salt thereof.

In a specific embodiment of the invention, R1 is a straight or branched chain, saturated or unsaturated hydrocarbyl group having from 10 to 18 carbon atoms; R2 is a C1-C2 alkyl group; A is an alkylene group containing from 2-4 carbon atoms; x is 1-20; and y is 0-5.

In another embodiment, R1 is a straight or branched chain, saturated or unsaturated hydrocarbyl group having from 12 to 18 carbon atoms; R2 is a methyl group; A is an alkylene group containing from 2-3 carbon atoms; x is 1-10; and y is 0-3, preferably 0.

In still another embodiment, the alkoxylated asymmetric amine of formula (I) has been quaternised and has the formula

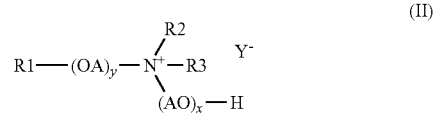

wherein R1 is a straight or branched chain, saturated or unsaturated hydrocarbyl group having from 8 to 24 carbon atoms; R2 is a C1-C4 alkyl group or a benzyl group; A is an alkylene group containing from 2-4 carbon atoms; x is 1-30; y is 0-10; R3 is a C1-C4 alkyl group; and $Y^-$ is a conventional anion, such as $Cl^-$ or the anion of methylsulphate.

However, the quaternised derivatives are less preferred because of their higher toxicity. Further, when using the compounds according to formula (I) as adjuvants, it is possible to obtain more concentrated formulations.

Specific examples of asymmetric alkylamine surfactants useful in the context of the present invention include, but are not limited to, (tallow alkyl)methylamine with 2 to 40 EO, preferably 5 to 20 EO, more preferably 7 to 12 EO; (coco alkyl)methylamine with about 2 to 40 EO, preferably 2 to 25, more preferably 2 to 20, still more preferably 2 to 15, and most preferably 2 to 10 EO; C12-alkyl methylamine with about 2 to 40 EO, preferably 2 to 25, more preferably 2 to 20, still more preferably 2 to 15, and most preferably 2 to 10 EO; 2-propylheptyl methylamine with 3 to 20 EO, preferably 4 to 15 EO, and most preferably 5 to 10 EO, compounds of formula I wherein R1 is (Exxal 13)-alkyl, R2 is methyl, y is 2, 3, 4 or 5, and x is 5-20, preferably 10-15, and compounds of formula I wherein R1 is C11-alkyl, R2 is methyl, y is 2, 3, 4 or 5, and x is 5-20, preferably 10-15.

The phenoxy acid herbicide preferably is a phenoxyacetic acid herbicide, phenoxybutyric acid herbicide, phenoxypropionic acid herbicide, aryloxy-phenoxypropionic acid herbicide, or a mixture thereof. The most preferred phenoxy acid herbicides are 4-CPA, 2,4-D, 3,4-DA, MCPA. MCPA-thioethyl, 4-CPB, 2,4-DB, 3,4-DB, MCPB, cloprop, 4-CPP, dichlorprop dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, and mixtures thereof.

In addition to the adjuvants mentioned here, the herbicidal formulations of the present invention can contain additional components including, but not limited to, additional surfactants or other additives. It is preferred that when the formulations of the invention do contain such additional components, such additional components are substantially non-irritating to the eye, substantially non-toxic to aquatic life, and have acceptable bio-efficacy. Such additional components include surfactants such as cationic, anionic, nonionic, and amphoteric surfactants. Examples of these surfactants are disclosed in McCutcheon's *Emulsifiers and Detergents*, North America Edition, 2000.

Non-limiting examples of preferred cationic surfactants are alkoxylated alkylamine and its quaternary derivative, alkoxylated etheramine and its quaternary derivative, alkylamine oxide, alkyl amidopropyl amine oxide, alkyl trimethyl ammonium chloride, and alkyl amidopropyl dimethylamine.

Non-limiting examples of preferred anionic surfactants are alkyl sulfate, alkyl ether sulfate, alkylsulfonate, alkylsulfosuccinate, alkoxylated phosphate ester, alkyl alpha-olefin sulfonate, alkyl n-methyl taurate, fatty acid isethionate, and alkyl ether carboxylate.

Non-limiting examples of preferred nonionic surfactants are sorbitan ester and its alkoxylated derivative, sorbitol ester and its alkoxylated derivative, fatty acid ester, castor oil alkoxylate, alcohol alkoxylate, alkanolamide, alkanolamide alkoxylate, and alkyl polyglycoside. Non-limiting examples of preferred amphoteric surfactants are alkyl betaine, alkyl amidopropyl betaine, alkyl amphoacetate, alkyl amphodiacetate, alkyl amphocarboxylate, alkyl amphopropionate, alkyl amphodipropionate, alkyl amidoamine carboxylate, alkyl amphohydroxypropyl sulfonate, alkyl sultaine, alkyl amidopropyl hydroxyl sultaine, alkyl dihydroxyethyl glycinate, alkyl aminopropionate, and blends thereof.

The pH of aqueous formulations according to the invention can vary, and is suitably in the range of 2-11, preferably 3-9, and most preferably 4-8. If only a part of the acid is neutralised by the amine surfactant, an additional alkaline component, e.g. a smaller amine, ammonia or KOH, may be used to modify the pH to the desired value. Preferred pH-modifiers are short-chain amine compounds, such as dimethylamine, isopropylamine, triethylamine or diethanolamine.

An advantage of formulating 2,4-D acid together with both an amine surfactant and a small amine, for example dimethylamine, is that it is possible to obtain very concentrated formulations without formulation instability and with a balanced amount of amine surfactant adjuvant. All the adjuvant-containing formulations in the example below have the same concentration of 2,4-D acid (600 g/l ae) as for example the commercially available 2,4-D dimethylamine salt formulations where no surfactant adjuvant is present in the formulation. Another advantage with formulating 2,4-D acid and water with the amine surfactants according to formula (I), or with a mixture of surfactants (I), small amines, and other additives, is the ease of preparation. The components form a non-viscous, clear formulation regardless of addition order, just by stirring at room temperature. If desired, heating may be used to speed up the homogenisation process. A convenient procedure for making a phenoxy acid salt solution is as follows: Phenoxy acid, surfactant adjuvant, dimethylamine or any other amine of low molecular weight, and water are added to a blending vessel and stirred at room temperature or with slight heating (up to 60° C.) until homogeneous. An additional amount of the amine of low molecular weight is added to adjust the pH of the formulation (measured on a 1% solution of the formulation in water) to 4.5-5.5, rendering the formulation water-soluble.

The compositions according to the invention may be concentrates without added water, concentrates with added water, or diluted, "ready to use", solutions. The amine salts may be produced without added water and other solvents and yet be in a liquid form at room temperature. This will normally be the case when the molar amount of herbicide exceeds the molar amount of amine adjuvant. The non-aqueous amine salt compositions, depending on the ratio of phenoxy acid herbicide to amine adjuvant, may be soluble in water as well as in oil. If the phenoxy acid composition is oil-soluble, the amine surfactants can mediate emulsification in water when said composition is diluted to an acceptable application concentration. The amine surfactants can thereby reduce or exclude the need for other types of emulsifiers in the composition.

The concentrations of the components may vary within wide limits, and a herbicide formulation may contain 0.01-99.9% by weight of a phenoxy acid herbicide and an amount of 0.01-70% by weight of a compound of formula (I) according to the invention.

As a water solution concentrate, the concentrations are normally in the range of 4-70%, preferably 20-40%, for the herbicide and 2-50%, preferably 2-20%, for the adjuvants, whereas for the ready-to-use solutions the corresponding ranges are 0.01-4% and 0.01-4%. The components may be mixed in the concentrate or be tank-mixed just before spraying the solution.

The concentrated herbicidal compositions according to the present invention preferably contain
a) 100-800 g ae/l of phenoxy acid herbicide
b) 25-400 g/l of adjuvant of formula (I)

The weight ratio of phenoxy acid to the alkoxylated asymmetric alkylamine surfactant of the invention is between 1:2 and 25:1 (i.e. the ratio between the weight of the ae of the herbicide and the weight of the amine surfactant). Typically, the weight ratio of phenoxy acid to the alkoxylated asymmetric alkylamine surfactant of the invention is between 2.5:1 and 20:1, more typically between 3:1 and 15:1.

A herbicidal composition according to the invention may optionally comprise other additives such as ammonium sulfate, potassium sulfate, potassium chloride, sodium sulfate, urea, glycerol, glycols, polyglycols, or mixtures thereof. A contemplated composition may optionally include a synergist, a quick-burn additive, a humectant, a co-herbicide, other pesticides, other amine compounds, e.g. dimethylamine, isopropylamine, triethylamine, or diethanol-amine, a dye, a pigment, a corrosion inhibitor, a thickener, a dispersing agent, a sequestrant, a defoamer, antifreeze, a pour-point depressant, anti-gelling agents, pH-modifiers, preservatives, hydrotropes, solvents, oils, process aids, or mixtures thereof. Combinations of phenoxy acid salts and co-herbicide salts are specifically contemplated by the present invention. Preferably, the additives used in the phenoxy acid compositions of the present invention possess sufficient solubility or dispersibility in a concentrated aqueous phenoxy acid solution at a pH of from about 4 to about 7 to allow desired concentrations to be attained.

Compositions of the present invention generally may be prepared by mixing the phenoxy acid salt solution together with other ingredients in a suitable mixing vessel with agitation, such as a blender.

This invention also relates to a herbicidal method of using a composition according to the invention in an amount effective to kill or control unwanted vegetation by diluting the composition in water and applying the diluted composition to foliage of the vegetation to be killed or controlled.

The phenoxy acid formulation of the invention should be applied to plant foliage at an application rate sufficient to give the desired effect. Application rates are usually expressed as amount of phenoxy acid (g ae) per unit area of land treated, e.g. grams ae per hectare (g ae/ha). What constitutes a "desired effect" varies according to the standards and practice of those who investigate, develop, market, and use phenoxy acid products. For example, the amount of phenoxy acid ae applied per unit area to give, consistently and reliably, at least 85% control of a plant species as measured by growth reduction or mortality is often used to define a commercially effective rate.

Preferred compositions of the invention provide enhanced herbicidal efficacy by comparison with commercial standard formulations of phenoxy acids. "Herbicidal efficacy," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific phenoxy acid composition, such as a composition of the present invention, is within the skill of the ordinary agricultural scientist. Those skilled in the art will likewise recognise that individual plant conditions, weather, and growing conditions, as well as the specific formulation selected, will influence the degree of biological effectiveness achieved in practising this invention. Useful application rates can therefore depend upon all of the above conditions. Much information is known about appropriate application rates for phenoxy acid formulations in general.

Various application methods may be employed, including broadcast spraying, directed spraying, or wiping the foliage with a diluted composition of this invention. Depending on the degree of control desired, the age and species of the plants, weather conditions and other factors, typically the phenoxy acid application rate is a herbicidally effective amount of about 0.1 to about 10 kg ae/ha and preferably from about 0.25 to about 2.5 kg ae/ha, although greater or lesser amounts may be applied.

Although it is an important objective of the invention to provide surfactants suitable for producing stable high load aqueous liquid concentrates comprising salts of phenoxy acids, it will be understood that the surfactants of the invention can also be used in solid phenoxy acid and phenoxy acid salt formulations.

The present invention will now be illustrated by the following nonlimiting examples.

Example 1

In this example, the superior biodegradability of the alkoxylated asymmetric alkylamine surfactants according to the invention compared to their di-ethoxylate counterparts is exemplified. The biodegradation data is shown in FIGS. 1 and 2.

In FIG. 1 the percentage of biodegradation of Polyoxyethylene (15) coco amine (Ethomeen C/25; reference) (■) and Polyoxyethylene (15) alkyl (C12-14) methylamine (ratio of alkyl chain lengths comparable to coco alkyl) (□), is plotted versus the time in prolonged Closed Bottle tests.

Figure 2:
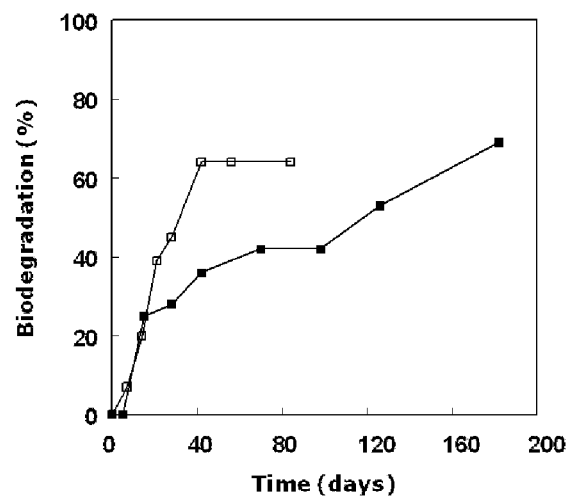
FIG. 2 is a graph showing percentages of biodegradation of Polyoxyethylene (15) tallow amine, hydrogenated (reference), and Polyoxyethylene (15) alkyl(C16-18) methylamine plotted versus time in an embodiment.

Similarly, in FIG. 2 the percentage of biodegradation of Polyoxyethylene (15) tallow amine, hydrogenated (Ethomeen HT/25; reference) (■), and Polyoxyethylene (15) alkyl($C_{16-18}$) methylamine (ratio of alkyl chain lengths comparable to tallow alkyl) (□), is plotted versus time in prolonged Closed Bottle tests.

The Closed Bottle tests were performed according to slightly modified official Test Guidelines (OECD 1982 Guideline for Testing of Chemicals, Degradation and Accumulation, No. 301 D: Ready biodegradability, Closed Bottle Test, Paris Cedex France; OECD 1992 Guideline for Testing of Chemicals, Degradation and Accumulation, No. 301: Ready Biodegradability, Paris Cedex France; EEC 1984 *Official Journal of the European Communities* L251 1984 Sep. 19 Part C: "Methods for the Determination of Ecotoxicity, Method C.6. Degradation-Biotic Degradation, Closed Bottle Test").

The nutrient medium of the Closed Bottle test contained per liter of deionised water: 8.5 mg $KH_2PO_4$, 21.75 mg $K_2HPO_4$, 33.4 mg $Na_2HPO_4.2H_2O$, 22.5 mg $MgSO_4.7H_2O$, 27.5 mg $CaCl_2$, 0.25 mg $FeCl_3.6H_2O$. Ammonium chloride was omitted from the medium to prevent nitrification. Use was made of 2 (duplicate) or 3 (triplicate) bottles containing only inoculum, and 2 or 3 bottles containing test substance and inoculum. The concentration of the test substances in the bottles was 2.0 mg/L. The inoculum was diluted to 2 mg DW/L in the closed bottles. Each of the prepared solutions was dispensed into the respective group of BOD bottles, so that all bottles were completely filled without air bubbles. The bottles were closed and incubated in the dark.

The biodegradation of polyoxyethylene(15)alkyl($C_{12-14}$) methylamine (ratio of alkyl chain length comparable to hydrogenated coco alkyl) and polyoxy-ethylene(15)alkyl ($C_{16-18}$)methylamine (ratio of alkyl chain length comparable to hydrogenated tallow alkyl) was measured by following the course of the oxygen decrease in the bottles with a special funnel using the method described above (C G van Ginkel and C A Stroo, "Simple Method to Prolong the Closed Bottle Test for the Determination of the Inherent Biodegradability", *Ecotoxicol Environ Saf.* 24 319-327 (1992)).

The dissolved oxygen concentrations were determined electrochemically using an oxygen electrode (WTW Trioxmatic EO 200) and meter (WTW OXI 530) (Retsch, Ochten, The Netherlands). The pH was measured using a Knick 765 calimatic pH meter (Elektronische Messgerate GmbH, Berlin, Germany). The temperature was measured and recorded with a thermocouple connected to a data logger. The dry weight (DW) of the inoculum was determined by filtrating 50 ml of the activated sludge over a preweighed 12 mm Schleicher and Schüll filter.

This filter was dried for 1.5 hours at 104° C. and weighed after cooling. DW was calculated by subtracting the weighed filters and by dividing this difference by the filtered volume.

The ThOD of the test substances was calculated from their molecular formulae and molecular weights, as follows.

$$ThOD_{NHB}(\text{mgO}_2/\text{mg}) = \frac{16\left(2C + \frac{1}{2}(H - Cl - 3N) + 3S + 2\frac{1}{2}P + \frac{1}{2}Na - O\right)}{MW}$$

Provided that the oxygen concentrations in all bottles at the start of the test were equal, the amounts of oxygen consumed in the bottles were calculated as follows: Oxygen consumption$_n$ (mg/L)=$M_c$−$M_t$ $M_t$=the mean oxygen concentration in the bottles containing the test compound and inoculated with activated sludge n days after the start of the test.

$M_c$=the mean oxygen level in the control bottle inoculated with activated sludge n days after the start of the test.

The biological oxygen demand (BOD) mg/mg of the test compound was calculated by dividing the oxygen consumption by the concentration of the test substance in the closed bottle. The biodegradation was calculated as the ratio of the biochemical oxygen demand (BOD) to the theoretical oxygen demand (ThOD).

Example 2

The ethoxylated secondary amines of the invention also demonstrate good bioefficacy compared to the prior art counterparts. The bioefficacy results are shown in the following Tables 2-3, where a formulation containing an adjuvant according to the invention (formulation 1; see Table 1) is compared to a formulation containing a tallow amine ethoxylate (formulation A; see Table 1)

In the provided example the herbicidal efficacy of 2,4-D formulations on *Brassica Napus* is presented.

Formulations were made up according to the scheme presented in Table 1. 2,4-D acid, surfactant adjuvant, dimethylamine (ex Fluka), and water were added to a blending vessel and stirred at room temperature or with slight heating (up to 60° C.) until homogeneous. The amount of surfactant was the same in all formulations, whereas the addition of dimethylamine varied between the formulations. Dimethylamine was added to adjust the pH of the formulation (measured on a 1% solution of the formulation in water) to 4.5-5.5, rendering the formulation water-soluble. After preparation the formulations were sent for greenhouse testing.

Three different doses of the formulations were applied to different sets of plants, containing 100, 200 and 400 g of 2,4-D acid per hectare, respectively. The formulations were diluted in tap water and applied as 200 liters of diluted spray solution per hectare. The aqueous herbicide formulations were sprayed on the plants by using a laboratory track sprayer fitted with a Lurmark "DIF 80" nozzle, set up to deliver 200±20 L/ha using gear 4 with a pressure of 210 Pa (30 psi). A calibration run was made with two Petri dishes containing paraffin oil at 1 m apart. The mean value obtained was 196 L/ha.

The results 21 days after treatment are collected in Table 2 and the results 30 days after treatment are collected in Table 3.

The results are weighted averages of three replicates.

The experiments were assessed according to the amount of green life growth and regrowth 21 days and 30 days after spraying for *Brassica napus*. A visual score of 0-100% was used, where 100% is all totally dead plants (100 percent control), and for example a 50% reduction in the amount of green growth present was scored by a comparison to the best untreated plant, the latter scoring 0% (0 percent control).

TABLE 2

The herbicidal activity (percent control) on *Brassica Napus* (Rapeseed), 21 days after treatment

| | Herbicide dose (g ae ha$^{-1}$) | | | | | |
|---|---|---|---|---|---|---|
| | 100 | ±S.E.* | 200 | ±S.E.* | 400 | ±S.E.* |
| Formulation 1 | 53.3 | 1.7 | 66.7 | 6 | 91.7 | 8.3 |
| Formulation A (comparison) | 46.7 | 1.7 | 56.7 | 1.7 | 81.7 | 1.7 |

*S.E. = standard error 100 g ae ha$^{-1}$ = 34 g ha$^{-1}$ of surfactant = 0.02% (w/w) in 200 liters of spray solution 200 g ae ha$^{-1}$ = 68 g ha$^{-1}$ of surfactant = 0.03% (w/w) in 200 liters of spray solution 400 g ae ha$^{-1}$ = 136 g ha$^{-1}$ of surfactant = 0.07% (w/w) in 200 liters of spray solution

TABLE 1

| Formulation | Surfactant | Amount of surfactant (g/l) | Amount of 2,4-D acid (g/l) | Amount of dimethyl-amine (30%) (g/l) | Amount of water |
|---|---|---|---|---|---|
| 1 | Ethoxylated (15 EO) monomethyl (C$_{16}$-C$_{18}$) alkyl amine | 204 | 600 | 266.4 | Balance up to 1 liter |
| Example of prior art: | | | | | |
| A (comparison) | Ethoxylated (16 EO) tallow amine | 204 | 600 | 266.4 | Balance up to 1 liter |

Note:
The pH of the formulations (1% in water) was adjusted to 4.5-5.5 using dimethylamine.

TABLE 3

The herbicidal activity (percent control) on *Brassica Napus* (Rapeseed), 30 days after treatment

| | Herbicide dose (g ae ha$^{-1}$) | | | | | |
|---|---|---|---|---|---|---|
| | 100 | ±S.E.* | 200 | ±S.E.* | 400 | ±S.E.* |
| Formulation 1 | 66.7 | 1.7 | 90 | 7.6 | 100 | 0 |
| Formulation A (comparison) | 61.7 | 1.7 | 75 | 2.9 | 96.7 | 3.3 |

*S.E. = standard error
100 g ae ha$^{-1}$ = 34 g ha$^{-1}$ of surfactant = 0.02% (w/w) in 200 liters of spray solution
200 g ae ha$^{-1}$ = 68 g ha$^{-1}$ of surfactant = 0.03% (w/w) in 200 liters of spray solution
400 g ae ha$^{-1}$ = 136 g ha$^{-1}$ of surfactant = 0.07% (w/w) in 200 liters of spray solution In the overall comparison of the formulations for the different doses it is found that formulation 1 performs better than the prior art formulation A.

It is shown in this example that the efficacy of 2,4-D on *Brassica Napus* can be enhanced by using surfactant adjuvants already at very low concentrations of surfactant. When 2,4-D is applied at 200 g per hectare, the surfactant concentration in the spray tank is only 0.03% (w/w), which is about one third of the generally recommended adjuvant dose in herbicidal formulations.

Because of the lower dosage rates needed, as well as the better biodegradability of the adjuvants themselves, the formulations according to the invention are ecologically preferred over conventional formulations.

The invention claimed is:

1. A herbicidal composition comprising at least one phenoxy acid herbicide or an agriculturally acceptable salt or derivative thereof, and a surfactant adjuvant, wherein said surfactant adjuvant comprises at least one alkoxylated asymmetric alkylamine surfactant of the formula

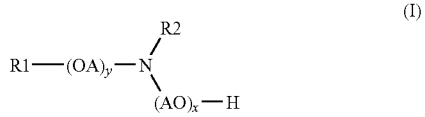

wherein R1 is a straight or branched chain, saturated or unsaturated hydrocarbyl group having from 8 to 24 carbon atoms; R2 is a $C_{1-4}$ alkyl group or a benzyl group; A is an alkylene group containing from 2-4 carbon atoms; x is 1-30; and y is 0-10; or a salt thereof.

2. The composition of claim 1 wherein R1 is a straight or branched chain, saturated or unsaturated hydrocarbyl group having from 10 to 18 carbon atoms; A is an alkylene group containing from 2-4 carbon atoms; x is 1-20; and y is 0-5.

3. The composition of claim 2 wherein R1 is a straight or branched chain, saturated or unsaturated hydrocarbyl group having from 12 to 18 carbon atoms; A is an alkylene group containing from 2-3 carbon atoms; x is 1-10; and y is 0-3.

4. The composition of claim 1 wherein said R1 is derived from a natural fatty acid.

5. The composition of claim 1 wherein said R1 group is derived from tallow.

6. The composition of claim 1 wherein said alkoxylated asymmetric alkylamine surfactant is selected from the group consisting of (tallow alkyl)methylamine with about 2 to 40 EO; (coco alkyl)methylamine with about 2 to 40 EO; $C_{12}$ methylamine with about 2 to 40 EO, 2-propylheptyl methylamine with 3 to 20 EO, compounds of formula I wherein R1 is methyl-branched $C_{13}$-alkyl, R2 is methyl, y is 2, 3, 4 or 5, and x is 5-20, and compounds of formula I wherein R1 is $C_{11}$-alkyl, R2 is methyl, y is 2, 3, 4 or 5, and x is 5-20.

7. The herbicidal composition of claim 1 wherein the phenoxy acid herbicide is a phenoxyacetic acid herbicide, phenoxybutyric acid herbicide, phenoxypropionic acid herbicide, aryloxyphenoxypropionic acid herbicide, or a mixture thereof.

8. The herbicidal composition of claim 1 where the phenoxy acid herbicide is selected from the group consisting of 4-CPA (4-chlorophenoxyacetic acid), 2,4-D ((2,4-dichlorophenoxy)acetic acid), 3,4-DA ((3,4-dichlorophenoxy)acetic acid), MCPA ((4-chloro-2-methylphenoxy)acetic acid, MCPA-thioethyl, 4-CPB (4-chlorophenoxybutyric acid), 2,4-DB ((2,4-dichlorophenoxy)butyric acid, 3,4-DB ((3,4-dichlorophenoxy)butyric acid), MCPB ((4-chloro-2-methylphenoxy)butyric acid), cloprop, 4-CPP (4-chlorophenoxypropionic acid), dichlorprop dichlorprop-P, 3,4-DP (3,4-dichlorophenoxypropionic acid), fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, and mixtures thereof.

9. The composition of claim 8 wherein said phenoxy acid herbicide is a water-soluble 2,4 D salt.

10. The composition of claim 9 wherein the concentration of phenoxy acid is in the range of 100-800 g ae/l and the ratio of phenoxy acid (wt % ae) to the surfactant adjuvant of formula I is from about 1:2 to about 25:1.

11. The composition of claim 10 wherein the concentration of phenoxy acid is in the range of 400-700 g ae/l and the ratio of phenoxy acid (wt % ae) to the surfactant adjuvant of formula I is from about 2.5:1 to about 20:1.

12. The composition of claim 11 wherein the ratio of phenoxy acid (wt % ae) to the surfactant adjuvant of formula I is from about 3:1 to about 15:1.

13. The composition of claim 1 which additionally comprises at least one co-herbicide.

14. The composition of claim 1 wherein said composition does not contain any water-insoluble solvent or water-insoluble oil.

15. The composition of claim 1 further comprising an alkaline compound other than the compound of formula (I).

16. The composition of claim 15 wherein the alkaline compound is selected from the group consisting of dimethylamine, isopropylamine, triethylamine and diethanolamine.

17. The composition of claim 1 wherein said composition is a solid phenoxy acid salt formulation.

18. The composition of claim 1 wherein said composition is an aqueous concentrate, wherein said aqueous concentrate contains a phenoxy acid equivalent in the range of from 20 to 40%, and from about 2 to about 20% of alkoxylated asymmetric alkylamine surfactant.

19. A method of controlling unwanted vegetation, said method comprising applying an effective amount of the herbicidal composition of claim 1 to said unwanted vegetation.

20. The method of claim 19 wherein said herbicidal composition comprises the phenoxy acid herbicide 2,4 D.

21. The composition of claim 1 wherein said alkoxylated asymmetric alkylamine surfactant is selected from the group consisting of (tallow alkyl)methylamine with, 5 to 20 EO; (coco alkyl)methylamine with about 2 to 25 EO; $C_{12}$ methylamine with about 2 to 25 EO, 2-propylheptyl methylamine with 4 to 15 EO, compounds of formula I wherein R1 is methyl-branched $C_{13}$-alkyl, R2 is methyl, y is 2, 3, 4 or 5, and x is 10-15, and compounds of formula I wherein R1 is $C_{11}$-alkyl, R2 is methyl, y is 2, 3, 4 or 5, and x is 10-15.

22. The composition of claim 1 wherein said alkoxylated asymmetric alkylamine surfactant is selected from the group consisting of (tallow alkyl)methylamine with 7 to 12 EO; (coco alkyl)methylamine with about 2 to 15 EO; $C_{12}$ methylamine with about 2 to 15 EO, 2-propylheptyl methylamine with 4 to 15 EO, compounds of formula I wherein R1 is methyl-branched $C_{13}$-alkyl, R2 is methyl, y is 2, 3, 4 or 5, and x is 10-15, and compounds of formula I wherein R1 is $C_{11}$-alkyl, R2 is methyl, y is 2, 3, 4 or 5, and x is 10-15.

23. The composition of claim 1 wherein said alkoxylated asymmetric alkylamine surfactant is selected from the group consisting of (tallow alkyl)methylamine with 7 to 12 EO; (coco alkyl)methylamine with about 2 to 10 EO; $C_{12}$ methylamine with about 2 to 10 EO, 2-propylheptyl methylamine with 5 to 10 EO, compounds of formula I wherein R1 is methyl-branched $C_{13}$-alkyl, R2 is methyl, y is 2, 3, 4 or 5, and x is 10-15, and compounds of formula I wherein R1 is $C_{11}$-alkyl, R2 is methyl, y is 2, 3, 4 or 5, and x is 10-15.

\* \* \* \* \*